United States Patent [19]

Demler et al.

[11] 4,243,822

[45] Jan. 6, 1981

[54] PROCESS FOR THE MANUFACTURE OF 4,4′ DIHYDROXYDIPHENYL

[75] Inventors: Walter R. Demler, Hamburg; Krishen L. Nagpal, Williamsville; Richard M. Dollard, W. Seneca; Eugene Odin, Williamsville; Donald T. Donahue, Kenmore, all of N.Y.

[73] Assignee: Buffalo Color Corporation, West Paterson, N.J.

[21] Appl. No.: 71,572

[22] Filed: Aug. 31, 1979

[51] Int. Cl.³ ........................... C07C 4/02; C07C 2/58
[52] U.S. Cl. ..................................... 568/769; 568/730
[58] Field of Search ........................ 568/730, 769, 770

[56] References Cited

U.S. PATENT DOCUMENTS

| | | | |
|---|---|---|---|
| 2,353,237 | 7/1944 | Harris | 568/769 |
| 2,368,361 | 1/1945 | Jenkins | 568/730 |
| 2,736,754 | 2/1956 | Webb | 568/769 |

FOREIGN PATENT DOCUMENTS 1951797 10/1968 Fed. Rep. of Germany ........... 568/769

Primary Examiner—John F. Niebling

[57] ABSTRACT

A process for the preparation of 4,4′ dihydroxydiphenyl by acidifying an alkali metal salt of 4,4′ dihydroxydiphenyl. The alkali metal salt of 4,4′ dihydroxydiphenyl is prepared by fusion of an alkali metal hydroxide with alkali metal diphenyl 4,4′ disulfonic acid. Because the reaction may be carried out in granular form, or in a reaction which is made highly fluid by using potassium hydroxide with potassium diphenyl 4,4′ disulfonic acid, or by reacting the alkali metal 4,4′ disulfonic acid in increments with the hydroxide, low molar ratios of hydroxide to alkali metal diphenyl 4′4, disulfonic acid may be used. When potassium diphenyl 4,4′ disulfonic acid is used in accordance with the invention, it is prepared by reacting 4,4′ diphenyl disulfonic acid with an inorganic neutral potassium salt.

44 Claims, No Drawings

PROCESS FOR THE MANUFACTURE OF 4,4' DIHYDROXYDIPHENYL

BACKGROUND OF THE INVENTION (A) Field of the Invention

This invention relates to a process for the manufacture of 4,4' dihydroxydiphenyl (biphenol, diphenol) from diphenyl and more particularly relates to such process wherein diphenyl is sulfonated followed by fusion of a sulfonate with a metal hydroxide to form 4,4' dihydroxydiphenyl salt which is acidified to form free 4,4' dihydroxydiphenyl.

(B) History of the Prior Art

Biphenol is useful as a reactant in condensation polymerizations and is particularly useful in forming phenolic type resins having good temperature resistance.

Biphenol was formed in the prior art by various unsatisfactory, complex and uneconomical methods. For example, halogenated diphenyl could be hydrolyzed (U.S. Pat. No. 3,413,341) or diphenyl could possibly be directly hydroxylated with peroxide in the presence of a suitable catalyst (U.S. Pat. No. 3,453,332).

One of the most suitable prior art methods for the preparation of biphenol is disclosed in U.S. Pat. No. 2,368,361 wherein diphenyl is sulfonated to form diphenyldisulfonic acid which is then reacted with sodium hydroxide or sodium salt to form a diphenyldisulfonic acid salt followed by fusion of the diphenyldisulfonic acid salt with an alkali metal hyroxide to form the sodium salt of biphenol followed by quenching in water and acidification to form biphenol. In general, low molar ratios of hydroxide to diphenyl disulfonic acid salt in the fusion were not previously believed possible or at least not desirable since in the absence of substantial excesses of alkali metal hydroxides in the fusion or in the absence of undesirable compounds such as benzene sulfonates to increase fusion fluidity, the reaction mass is solid or almost solid at low enough reaction temperatures to prevent product decomposition since the melting temperature of the alkali metal salts of diphenyl disulfonic acid is above the decomposition temperature of the biphenol salt reaction product.

The process disclosed in U.S. Pat. No. 2,368,361 is an example of such an unsatisfactory process since benzene or another aromatic hydrocarbon of relatively low boiling point is required to be sulfonated subsequent to sulfonation of diphenyl. The resulting benzenesulfonic acid or other sulfonic acid of a low boiling aromatic hydrocarbon permits the fusion to be carried out solely in sodium hydroxide which, previously at low molar ratios in the absence of the additional sulfonic acid or sulfonic acid salt, did not yield fusions which were as fluid and efficient as desirable. U.S. Pat. No. 2,368,361 indicates that the presence of benzenesulfonate permits sodium hydroxide to be present in the fusion in a molar ratio of between 3:1 and 4:1 to sulfonic acid groups in the fusion. The patent fails to directly point out that over half of the sulfonic groups are provided by undesirable benzenesulfonate rather than diphenyldisulfonic acid which is the intermediate to biphenol. The method disclosed in U.S. Pat. No. 2,368,361 therefore requires large quantities of sodium hydroxide in the fusion which are not actually utilized in the formation of the sodium salt of 4,4' dihydroxydiphenyl (biphenol sodium salt). In Example 1 of the patent, in the best case, i.e., 65 grams of NaOH and 44 grams of disulfonate (44 out of 100 total sulfonates), there are about 11.4 moles of sodium hydroxide provided for each mole of diphenyldisulfonic acid salt in the fusion. In addition, at the high fusion temperatures of 350° to 370° C., it is believed that at least some decomposition of the sodium biphenol salt product occurs.

After formation, the process set forth in U.S. Pat. No. 2,368,361 still requires steps to separate biphenol from the phenols resulting from fusion of the benzene sulfonates. The process therefore wastes benzene, wastes sodium hydroxide and is exceedingly complex.

It has been suggested that the potassium salt of diphenyldisulfonic acid could be used in fusion with potassium hydroxide which would lend fluidity to the fusion thus permitting lower mole ratios of potassium hydroxide to be used. Unfortunately, potassium salts of sulfonic acids usually are formed by neutralizing the sulfonic acid with costly potassium hydroxide in order to obtain a good yield of the salt. Potassium hydroxide, is generally formed by electrolytic means from the much more readily available and less costly inorganic potassium salts such as potassium chloride.

BRIEF DESCRIPTION OF THE INVENTION

The invention is an improved process for the preparation of the alkali metal salt of 4,4' dihydroxydiphenyl (biphenol alkali metal salt) by fusion reaction of an alkali metal hydroxide with an alkali metal diphenyl disulfonate. The major improvement in the process comprises providing a total of from about 4 to about 20 moles of hydroxide and preferably from about 4 to less than 6 moles of hydroxide to the fusion per mole of alkali metal diphenyldisulfonate provided to the fusion, i.e., 2 to less than 3 moles of hydroxide per mole of sulfonate groups. This improvement is permitted by different process steps discovered in accordance with the invention which can be used independently and often in combination to permit low molar ratios of hydroxide to disulfonate to be used in the preparation of biphenol without high reaction temperatures or undesirable additives. Most desirably, the hydroxide and alkali metal diphenyl disulfonate are provided and reacted in stochiometric quantities.

The reduced quantities of hydroxide required to manufacture biphenol is made possible by two general methods. The first method results from the unexpected discovery that the reaction may efficiently be conducted in such a way that the biphenol alkali metal salt product is a solid or semisolid and is preferably a granular solid thus the need for a fluid, i.e., pourable product, is entirely eliminated and the second method is to maintain high fusion fluidity in fluid type reactions without using undesirable and contaminating compounds to enhance fluidity and without using large quantities of either sodium or potassium hydroxide.

Solid or semisolid systems may efficiently be used either by forming granular shapes during the reaction or by mechanically granulating or pelletizing the product. Unexpectedly, granular alkali metal biphenol salt is formed when the hydroxide and alkali metal diphenyldisulfonate are initially provided in granular form and the fusion reaction temperature is carefully controlled to a temperature above the melting point of the alkali metal hydroxide but below the melting temperature of the alkali metal biphenol salt product. This temperature is usually between 295° and 342° C. When the granular reaction is used, less than 10 percent water or other solvent for the reactants, by weight of hydroxide should be present and the hydroxide should be present in a molar ratio to disulfonate of from 4:1 to less than 6:1.

When a continuous phase is used, i.e., non-granular uniform reaction mixture which may be a fluid, it has been discovered:

that temperatures of 342° to less than 350° C. and desirably less than 347° C. should preferably be used for best fluidity at the least decomposition;

that fluid continuous phase reactions can be obtained even at low molar ratios of hydroxide to alkali metal diphenyl disulfonates when both potassium hydroxide and potassium diphenyl disulfonate are incorporated into the fusion as alkali metal hydroxide and alkali metal diphenyldisulfonate respectively without wasting potassium hydroxide to prepare potassium diphenyldisulfonate by treating a solution of diphenyldisulfonic acid with a neutral inorganic potassium salt to precipitate the potassium diphenyl disulfonate.

Lower molar ratios of hydroxide to alkali metal diphenyl disulfonate, i.e., from 2 to 10, and preferably 2 to less than 6, moles of hydroxide per mole of alkali metal diphenyl disulfonate, can ultimately be used in both the solid and continuous phase reactions when the disulfonate salt is added in increments throughout the time period of the reaction. This discovery is especially suitable for continuous reactions for biphenol preparation.

DETAILED DESCRIPTION OF THE INVENTION

In accordance with this invention, there is provided a process which overcomes or reduces prior art disadvantages encountered in prior art methods for preparation of biphenol and its alkali metal salt. In particular, the methods of the invention waste less hydroxide, increase fusion fluidity where fluid fusions are used, decrease fusion temperature, do not require additives to enhance fluidity, reduce end product decomposition, result in biphenol products of high purity and may be carried out continuously.

Biphenol, as used herein, means 4,4' dihydroxydiphenyl having the structural formula:

I and is prepared by acidifying its alkali metal salt which acidification may be preceded by quenching in water.

The biphenol salt, i.e., the alkali metal salt of biphenol or dialkali metal diphenyl 4,4', dioxide has the structural formula:

II where M is an alkali metal selected from sodium, potassium and lithium.

The biphenol salt, in accordance with the present invention, is manufactured by fusion of 4,4' disulfonic and alkali metal (M) salt (alkali metal diphenyldisulfonate or alkali metal diphenyl 4,4' disulfonate) having the structural formula:

III with an alkali metal hydroxide.

The disulfonic acid alkali metal salt is made by treating the corresponding acid with hydroxide. The 4,4' disulfonic acid is usually made by sulfonation of diphenyl to form diphenyl 4,4' disulfonic acid by known methods. Diphenyl has the structural formula:

IV

As previously discussed, the improvements in the process in accordance with the present invention permit lower molar ratios of alkali metal hydroxide to alkali metal diphenyldisulfonate to be used in the fusion. The ratios are from 4 to about 20 and preferably from 4 to less than 6 moles of hydroxide per mole of disulfonate. This ratio is equivalent to from 2 to about 10 and preferably from 2 to less than 3 moles of hydroxide per mole of sulfonate groups in the fusion. A stochiometric quantity of hydroxide can be used which is 4 moles of hydroxide per mole of disulfonate composition in the fusion or 2 moles of hydroxide per mole of sulfonate groups in the fusion.

The hydroxide and alkali metal diphenyldisulfonate can be provided in granular form, i.e., preferably in particle sizes of from 0.1 to 2 millimeters and, when the reaction temperature is between 295° and 342° C. and the ratio of hydroxide to sulfonate groups is from 2 to 1 less than 3 to 1, the resulting 4,4' dihydroxydiphenyl alkali metal salt reaction product is in porous or granular form. 295° C. is about the minimum temperature for reaction and 342° C. is about the maximum temperature to prevent melting of the 4,4' dihydroxydiphenyl alkali metal product when the alkali metal is potassium. When the alkali metal in the product is sodium, temperatures up to 347° C. can be used.

It is believed that under these conditions, the alkali metal hydroxide melts and almost immediately reacts with the alkali metal diphenyl disulfonate to form the biphenol salt product which is solid at the reaction temperature. The speed of the reaction, especially at temperatures close to 342° C., is such that there is insufficient time to form a continuous uniform reaction mass.

At temperatures above 295° C. but below the melting temperature of biphenol salt product (believed to be about 342° C. for the potassium salt and above 360° C. for the sodium salt), especially in the presence of some excesses but not a large excess of hydroxide (e.g., a molar ratio of between 4:1 and 7:1 hydroxide to sulfonate groups), only the hydroxide melts thus forming a continuous phase, high viscosity, almost solid reaction mass containing melted hydroxide, solid biphenol salt product and solid alkali metal diphenyl disulfonate. It was not, however, realized that such a solid or semisolid reaction mass could produce an efficient reaction for preparation of a biphenol salt product which can be extruded or otherwise formed into particles.

When higher temperatures are used, e.g., above 342° C., it has now been discovered that the fluidity can be increased if desired without using large excesses of alkali metal hydroxides or undesirable additives such as monosulfonates, e.g., benzene sulfonate. It has, however, also been discovered that very high fusion temperatures, i.e., 350° C. or above, are to be avoided since it is believed that at least some decomposition of the 4,4' dihydroxydiphenyl alkali metal salt product occurs at 350° C. or above.

It is known that diphenyl 4,4' disulfonate acid is soluble in water but that alkali salts of this compound are insoluble in water. When potassium diphenyldisulfonate and potassium hydroxide are used in the fusion, low molar ratios of potassium hydroxide to diphenyl 4,4' disulfonic acid salt can be utilized while retaining fluidity. The loss of potassium hydroxide in neutralizing diphenyldisulfonic acid to obtain the potassium diphenyldisulfonate is avoided by taking advantage of the unusual insolubility of potassium diphenyldisulfonate by reacting potassium chloride or other neutral inorganic potassium salt with the disulfonic acid to precipitate the potassium diphenyldisulfonate which is used in the fusion.

In accordance with the preferred embodiment of the continuous phase fusion reaction of the present invention, from about 2 to about 10 moles, preferably from 2 to less than 3 moles and most preferably about 2 moles, i.e., a stoichiometric quantity of potassium hydroxide per mole of sulfonate groups in potassium diphenyldisulfonate is used in the fusion to form biphenol. In the prior art, it was recognized that usually at least about 7 moles of hydroxide per mole of sulfonate in the disulfonate was required. This is even substantially true when the supposedly improved process in accordance with U.S. Pat. No. 2,368,361 is used, since the additional benzene or other aromatic sulfonate in the fusion, as required by the exceedingly complicated process of that patent, still results in a high molar ratio of hydroxide to sulfonate groups.

In both the granular and continuous phase reactions, the fusion with alkali metal hydroxide (eg., the hydroxides of lithium, sodium and potassium) is usually carried out at from about 295° to about 347° C. over a time of from about 30 minutes to about 6 hours. The fluid reactions, at low molar ratios, use potassium salts and potassium hydroxide at a final temperature above about 342° C. Temperatures higher than 347° C. can be used but are not desirable due to decomposition of the 4,4' dihydroxydiphenyl alkali metal salt product.

In accordance with the present invention, the molar ratio of hydroxide to sulfonate groups, if not initially stoichiometric, may optionally be reduced toward stoichiometric quantities in either the granular or continuous phase fusion processes by adding additional alkali metal diphenyldisulfonate to the fusion after at least some and usually after most of the initial alkali metal diphenyldisulfonate has reacted. The adding of the additional alkali metal disulfonate to the fusion further reduces the total molar ratio of alkali metal hydroxide to alkali metal diphenyl 4,4' disulfonate by reacting with alkali metal hydroxide which previously did not react with the initial charge of alkali metal diphenyldisulfonate. In this way, the concentration of unreacted hydroxide at the end of the complete reaction may be reduced to less than 2, desirably less than 1 and as low as 0 remaining moles of unreacted hydroxide per mole of alkali metal in the 4,4' dihydroxydiphenyl salt product.

The reaction to prepare 4,4' dihydroxydiphenyl alkali metal salt, in accordance with any embodiment of the present invention, can be made continuous by stepwise or continuous addition of reactants.

In any case, where the alkali metal salt of 4,4' dihydroxydiphenyl is prepared, the free 4,4' dihydroxydiphenyl can be made by acidifying the salt with any suitable acid such as hydrochloric or sulfuric acid.

The following examples serve to illustrate and not limit the present invention. Unless otherwise indicated, all parts and percentages are by weight.

EXAMPLE 1

Potassium diphenyldisulfonate is prepared as previously described by treating diphenyldisulfonic acid with potassium chloride. The precipitated potassium diphenyldisulfonate is then dried. 1,400 grams of potassium hydroxide flakes containing 90% KOH and 10% water are melted by heating to between 240° and 260° C. 700 grams of the dried potassium diphenyldisulfonate are blended with the melted potassium hydroxide over a period of fifteen minutes. The mixture is then heated to between 335° and 340° C. for three hours. The mixture is then poured from the reaction vessel and cooled. 400 grams of the resulting reaction mass are dissolved in 1,200 cc's of water and filtered. The filtrate is adjusted to a pH of 2 with about 435 cc's of 32% HCl. The resulting precipitate is filtered and washed with 200 cc's of cold water and dried in a vacuum of about 25 inches at 70° C. The yield of the resulting biphenol after purification is about 85% of theoretical.

EXAMPLE 2

Example 1 is repeated except that subsequent to fusion for three hours at between 335° and 342° C., an additional 200 grams of potassium diphenyldisulfonate is added to the fusion and the fusion is permitted to react at a temperature of between 335° and 342° C. for an additional two hours. The additional potassium diphenyl 4,4' disulfonate is found to be converted to biphenol in high yield and the percentage of unreacted potassium hydroxide is substantially reduced.

EXAMPLE 3

Example 1 is repeated except that 840 grams of sodium diphenyl 4,4' disulfonate is used which is prepared without sodium hydroxide by treating diphenyldisulfonic acid with sodium chloride and 2100 grams of potassium hydroxide are used. About two thirds of the resulting product could be poured out. The yield after purification is 75%.

EXAMPLE 4

Example 3 is repeated except that 600 grams of the sodium diphenyldisulfonate and 2400 grams of sodium hydroxide are used. The resulting product is pasty with about one-half being pourable from the reactor. The yield is 74%.

EXAMPLE 5

Example 2 is repeated except 400 grams of potassium hydroxide flakes are used and prior to pouring, the temperature is raised to 347° C. which reduces viscosity.

EXAMPLE 6

Example 5 is repeated except sodium hydroxide is substituted for potassium hydroxide and sodium diphenyl 4,4' disulfonate is substituted for potassium diphenyl 4,4' disulfonate. No decrease in viscosity is noted upon raising the temperature to 347° C. nor is any such decrease noted as high as 355° C.

EXAMPLE 7

Granular potassium diphenyl 4,4' disulfonate and potassium hydroxide flakes are fused together at 335° C. in a mole ratio of 5 hydroxide to 1 disulfonate. The reaction mass never becomes fluid and after reaction is a highly porous biphenol salt solid which is easily broken into granules.

The foregoing examples are intended to illustrate but not limit improved processes of the invention wherein high yields of biphenol are obtained with a simple process requiring less use and waste of alkali metal hydroxide and lower reaction temperatures.

What is claimed is:

1. In a process for the preparation of the alkali metal salt of 4,4' dihydroxydiphenyl by fusion reaction of an alkali metal hydroxide with an alkali metal diphenyldisulfonate, the improvement which comprises providing a total of from 4 to less than 6 moles of hydroxide to the fusion per mole of alkali metal diphenyldisulfonate provided to the fusion said fusion being free from additivies to enhance fluidity.

2. The process of claim 1 wherein the hydroxide and alkali metal diphenyldisulfonate are provided and reacted in stoichiometric quantities.

3. The process of claim 1 wherein an initial portion of the alkali metal diphenyldisulfonate is provided at the commencement of the reaction and at least one additional portion is provided after commencement of the reaction.

4. The process of claim 1 wherein the reaction is carried out continuously.

5. The process of claim 1 wherein the hydroxide and alkali metal diphenyldisulfonate are provided in granular form and the reaction temperature is between 295° and 342° C.

6. A process for the preparation of 4,4' dihydroxydiphenyl alkali metal salt which comprises:
    (a) sulfonating diphenyl to form diphenydisulfonic acid;
    (b) reacting the diphenyldisulfonic acid with an inorganic compound to form an alkali metal diphenyldisulfonate;
    (c) fusing an alkali metal hydroxide with an initial charge of the alkali metal diphenyldisulfonate at a concentration of from 2 to about 10 moles of hydroxide per mole of sulfonate groups in the alkali metal disulfonate to form 4,4' dihydroxydiphenyl salt said fusion being free from additives to enhance fluidity; and
    (d) after most of the initial charge of alkali metal diphenyldisulfonate has reacted and when excess alkali metal hydroxide is present, adding additional alkali metal diphenyldisulfonate to the fusion to form additional 4,4' dihydroxydiphenyl salt by reaction with previously unreacted alkali metal hydroxide.

7. The process of claim 6 wherein sufficient additional alkali metal diphenyldisulfonate is added to reduce the concentration of unreacted hydroxide to less than 2 moles of hydroxide per mole of alkali metal in the 4,4' dihydroxydiphenyl salt product.

8. The process of claim 7 wherein sufficient additional alkali metal diphenyldisulfonate is added to reduce the concentration of unreacted hydroxide to less than one mole of hydroxide per mole of alkali metal in the 4,4' dihydroxydiphenyl salt product.

9. The process of claim 8 wherein the alkali metal diphenyldisulfonate is potassium diphenyldisulfonate, the hydroxide is potassium hydroxide and the fusion temperature is from about 295° C. to about 347° C.

10. A process for the preparation of 4,4' dihydroxydiphenyl alkali metal salt from an alkali metal diphenyldisulfonate which comprises:
    (a) fusing an alkali metal hydroxide with an initial charge of the alkali metal diphenyldisulfonate at a concentration of from about 10 moles of hydroxide per mole of sulfonate groups in the alkali metal disulfonate to form 4,4' dihydroxydiphenyl salt said fusion being free from additives to enhance fluidity; and
    (b) after most of the initial charge of alkali metal diphenyldisulfonate has reacted and when excess alkali metal hydroxide is present, adding additional alkali metal diphenyldisulfonate to the fusion to form additional 4,4' dihydroxydiphenyl salt by reaction with previously unreacted alkali metal hydroxide.

11. The process of claim 10 wherein from 2 to less than 3 moles of hydroxide per mole of sulfonate group are used.

12. A process for the preparation of 4,4' dihydroxydiphenyl potassium salt comprising:
    (a) sulfonating diphenyl to form diphenyldisulfonic acid;
    (b) reacting the diphenyldisulfonic acid with a water soluble inorganic neutral potassium salt to precipitate potassium diphenyl 4,4' disulfonate; and
    (c) fusing potassium hydroxide with an initial charge of the potassium diphenyldisulfonate at a concentration of from about 2 to about 10 moles of hydroxide per mole of sulfonate groups in the potassium diphenyldisulfonate to form 4,4' dihydroxydiphenyl potassium salt said fusion being free from additives to enhance fluidity.

13. The process of claim 12 wherein the inorganic potassium salt is potassium chloride and the initial molar concentration of potassium hydroxide is from 2 to less than 3 moles per mole of sulfonate group in the potassium diphenyl 4,4' disulfonate.

14. The process of claim 13 wherein the fusion is heated to from about 295° C. to about 347° C. over a time of from about 30 minutes to about 6 hours and to a final temperature to obtain maximum fluidity of from 343° to 347° C.

15. The process of claim 12 wherein after reaction of most of the initial charge of potassium diphenyldisulfonate and when excess potassium hydroxide is present, additional potassium diphenyl 4,4' disulfonate is added to the fusion to form additional 4,4' dihydroxydiphenyl salt by reaction with previously unreacted potassium hydroxide.

16. The process of claim 15 wherein sufficient additional potassium diphenyldisulfonate is added to reduce the concentration of unreacted potassium hydroxide to less than two moles of potassium hydroxide per mole of potassium in the 4,4' dihydroxydiphenyl salt product.

17. The process of claim 16 wherein sufficient additional potassium diphenyldisulfonate is added to reduce the concentration of unreacted potassium hydroxide to less than one mole of potassium hydroxide per mole of potassium in the 4,4' dihydroxydiphenyl salt product.

18. The process of claim 1 wherein the alkali metal salt of 4,4' dihydroxydiphenyl is acidified to form 4,4' dihydroxydiphenyl 19. The process of claim 2 wherein the alkali metal salt of 4,4' dihydroxydiphenyl is acidified to form 4,4' dihydroxydiphenyl.

20. The process of claim 3 wherein the alkali metal salt of 4,4' dihydroxydiphenyl is acidified to form 4,4' dihydroxydiphenyl.

21. The process of claim 4 wherein the alkali metal salt of 4,4' dihydroxydiphenyl is acidified to form 4,4' dihydroxydiphenyl.

22. The process of claim 5 wherein the alkali metal salt of 4,4' dihydroxydiphenyl is acidified to form 4,4' dihydroxydiphenyl.

23. The process of claim 6 wherein the alkali metal salt of 4,4' dihydroxydiphenyl is acidified to form 4,4' dihydroxydiphenyl.

24. The process of claim 8 wherein the alkali metal salt of 4,4' dihydroxydiphenyl is acidified to form 4,4' dihydroxydiphenyl.

25. The process of claim 9 wherein the alkali metal salt of 4,4' dihydroxydiphenyl is acidified to form 4,4' dihydroxydiphenyl.

26. The process of claim 10 wherein the alkali metal salt of 4,4' dihydroxydiphenyl is acidified to form 4,4' dihydroxydiphenyl.

27. The process of claim 11 wherein the alkali metal salt of 4,4' dihydroxydiphenyl is acidified to form 4,4' dihydroxydiphenyl.

28. The process of claim 12 wherein the alkali metal salt of 4,4' dihydroxydiphenyl is acidified to form 4,4' dihydroxydiphenyl.

29. The process of claim 13 wherein the alkali metal salt of 4,4' dihydroxydiphenyl is acidified to form 4,4° dihydroxydiphenyl.

30. The process of claim 14 wherein the alkali metal salt of 4,4' dihydroxydiphenyl is acidified to form 4,4' dihydroxydiphenyl.

31. The process of claim 15 wherein the alkali metal salt of 4,4' dihydroxydiphenyl is acidified to form 4,4' dihydroxydiphenyl.

32. The process of claim 17 wherein the alkali metal salt of 4,4' dihydroxydiphenyl is acidified to form 4,4' dihydroxydiphenyl.

33. The process of claim 6 wherein the process is carried out continuously.

34. The process of claim 8 wherein the process is carried out continuously.

35. The process of claim 9 wherein the process is carried out continuously.

36. The process of claim 10 wherein the process is carried out continuously.

37. The process of claim 11 wherein the process is carried out continuously.

38. The process of claim 12 wherein the process is carried out continuously.

39. The process of claim 13 wherein the process is carried out continuously.

40. The process of claim 14 wherein the process is carried out continuously.

41. The process of claim 15 wherein the process is carried out continuously.

42. The process of claim 17 wherein the process is carried out continuously.

43. The process of claim 23 wherein the process is carried out continuously.

44. The process of claim 26 wherein the process is carried out continuously.

* * * * *